United States Patent [19]
Saigo et al.

[11] Patent Number: 6,159,891
[45] Date of Patent: Dec. 12, 2000

[54] CATALYST FOR BISALKOXYCARBONYLATION OF OLEFINS, AND METHOD FOR PRODUCTION OF SUCCINATE DERIVATIVES

[75] Inventors: Kazuhiko Saigo; Yukihiko Hashimoto; Minoru Hayashi, all of Tokyo, Japan

[73] Assignee: Daicel Chemical Industries, Ltd., Osaka, Japan

[21] Appl. No.: 09/332,072

[22] Filed: Jun. 14, 1999

[51] Int. Cl.[7] .............................. B01J 31/24; B01J 31/28; B01J 31/30
[52] U.S. Cl. ..................... 502/162; 502/150; 502/152; 502/154; 502/155; 502/156; 502/165
[58] Field of Search ................... 502/150, 152, 502/154, 155, 156, 162, 165

[56] References Cited

U.S. PATENT DOCUMENTS

| | | | |
|---|---|---|---|
| 4,333,852 | 6/1982 | Warren | 568/700 |
| 4,414,160 | 11/1983 | Erpenbach et al. | 502/154 |
| 4,730,080 | 3/1988 | Drent | 502/102 |
| 5,030,712 | 7/1991 | Van Doorn et al. | 502/162 |
| 5,137,857 | 8/1992 | Van Doorn | 502/162 |

OTHER PUBLICATIONS

Journal of the American Chemical Society /98:7/Mar. 31, 1976 pp. 1806–1809.
Journal of Molecular Catalysis A:Chemical 111 (1996) L3–L6 No Month Available.
J. Chem. Soc. Perkin Trans. 1, (1993) pp. 1031–1037 No Month Available.
J. Org. Chem. (1992), 57, 4189–4194 No Month Available.
J. Org. Chem., vol. 37, No. 12, (1972) pp. 2034–2035 No Month Available.
Bull. Chem. Soc. Jpn 64, 3600–3606(1991) vol. 64, No. 12 No Month Available.
Tetrahedron Letters, vol. 28, No. 3, pp. 325–328, (1987) No Month Available.
Journal of the American Chemical Society /98:7/Mar. 31, 1976 pp. 1810–1823.
Angew.Chem. Int.Ed. Engl. (1993), 32 No. 12 pp. 1719–1720 No Month Available.
Organometallics (1992), 11, 1975–1978 No Month Available.
Bull. Chem. Soc. Jpn., 69, 735–742 (1996) No Month Available.
Tetrahedron Letters vol. 39, No. 41 Oct. 8, 1998 pp. 7529–7532.

*Primary Examiner*—Elizabeth Wood
*Attorney, Agent, or Firm*—Birch, Stewart, Kolasch & Birch, LLP

[57] ABSTRACT

A catalyst for the bisalkoxycarbonylation of olefins comprising a noble metal compound and a phosphine chalcogenide of the following formula (1):

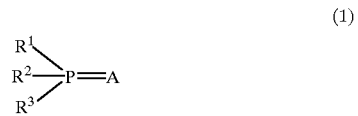

(1)

wherein each of $R^1$, $R^2$ and $R^3$ is, independently, an alkyl group or an aryl group each of which may have a substituent, and A is a Group 16 element of the Periodic Table; and $R^1$, $R^2$ or $R^3$ may be combined, directly or through a bridging group, with one another where the groups to be combined may be attached either to an identical phosphorus atom or to different phosphorus atoms. Element A includes oxygen, sulfur and selenium atoms. The noble metal compound includes palladium(II) halides and other palladium compounds. The catalyst may further include a copper (I) halide or other copper compound as a co-catalyst. The use of this catalyst can provide the bisalkoxycarbonylation of olefins with efficiency.

6 Claims, No Drawings

CATALYST FOR BISALKOXYCARBONYLATION OF OLEFINS, AND METHOD FOR PRODUCTION OF SUCCINATE DERIVATIVES

BACKGROUND OF THE INVENTION

1. Field of the Invention

The present invention relates to catalysts used for the bisalkoxycarbonylation of olefins, to novel phosphine chalcogenides which are useful as ligands of the catalysts, to processes for the bisalkoxycarbonylation of olefins using the catalysts, and to methods for production of succinate derivatives.

2. Description of the Prior Art

Processes for the alkoxycarbonylation of ole fins have been proposed in (1) J. Am. Chem. Soc., 98, 1806(1976); (2) J. Mol. Cat. A: Chemical 111, L3–L6(1996); (3) J. Chem. Soc. Perkin Trans., 1031(1993); (4) J. Org. Chem., 57, 4189(1992), and satisfactory results have been achieved by these processes.

For the bisalkoxycarbonylation of olefins, processes have been reported in documents (5) J. Org. Chem., 37, 2034 (1972),; (6) J. Am. Chem. Soc., 98, 1806(1976); (7) Bull. Chem. Soc. Jpn., 64, 3600(1991); (8) Tetrahedron Lett., 28, 325(1987); (9) J. Am. Chem. Soc., 98, 1810(1976); (10) Angew. Chem. Int. Ed. Engl., 32, 1719(1993); and (11) Organometallics, 11, 1975(1992). These processes are, however, respectively disadvantageous: The processes in the documents (5) and (6) are low in yield, the process in the document (7) gives a mixture of a monoalkoxycarbonylated compound and a bisalkoxycarbonylated compound, the process in the document (8) requires the addition of tetramethylurea or propylene oxide and ethyl ortho-acetate, the process in the document (9) should be conducted under high pressure conditions (3 atm), processes in the documents (10) and (11) accompany oligomerization.

In a document (12) Bull. Chem. Soc. Jpn., 69, 735(1996) is disclosed the use of an optically active bisoxazoline as a ligand in the bisalkoxycarbonylation to obtain an optically active substance. This process requires a long time for the reaction and is low in reactivity.

SUMMARY OF THE INVENTION

Accordingly, it is an object of the present invention to provide a catalyst which can catalyze the bisalkoxycarbonylation of olefins with efficiency.

It is another object of the invention to provide a novel phosphine chalcogenide compound which is useful as a ligand in a catalyst for the asymmetric bisalkoxycarbonylation of olefins.

A further object of the invention is to provide an efficient process for the bisalkoxycarbonylation of olefins.

It is a yet another object of the invention to provide a process by which corresponding succinate derivatives can be obtained from olefins in high yields under moderate conditions.

The present inventors made intensive investigations to achieve the above objects, and found that the use of a noble metal compound catalyst including a phosphine chalcogenide as a ligand can catalyze the bisalkoxycarbonylation of olefins with efficiency. The invention has been accomplished based upon the finding.

To be more specific, the invention provides, in an aspect, a catalyst for the bisalkoxycarbonylation of olefins comprising a phosphine chalcogenide and a noble metal compound, the phosphine chalcogenide being of the following formula (1):

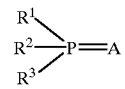

(1)

wherein $R^1$, $R^2$ and $R^3$ are, independently, an alkyl group or an aryl group each of which may have a substituent, and A is a Group 16 element of the Periodic Table; $R^1$, $R^2$ or $R^3$ may be combined, directly or through a bridging group, with one another where the groups to be combined may be attached either to an identical phosphorus atom or to different phosphorus atoms.

The element A may include, for example, an oxygen atom, a sulfur atom and a selenium atom. As examples of the phosphine chalcogenide, there maybe mentioned triphenylphosphine oxide, triphenylphosphine sulfide, triphenylphosphine selenide, 2,2'-bis(diphenylthiophosphoryl)-1,1'-binaphthyl, 2,3-bis(diphenylthiophosphoryl)butane, and 2,3-O-isopropylidene-2,3-dihydroxy-1,4-bis(diphenylthiophosphoryl)butane. The noble metal compound may include palladium compounds, for instance.

The catalyst for the bisalkoxycarbonylation of olefins may further include a co-catalyst such as a copper catalyst. By way of illustration, the catalyst can include a palladium(II) halide as a noble metal compound and a copper(I) halide as a co-catalyst.

The present invention provides, in another aspect, an optically active 2,2'-bis(diphenylchalcogenophosphoryl)-1,1'-binaphthyl of the following formula (1a):

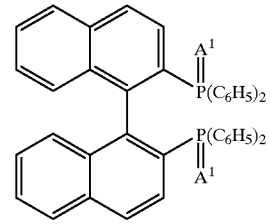

(1a)

wherein $A^1$ is a Group 16 element of the Periodic Table other than oxygen; an optically active 2,3-bis(diphenylchalcogenophosphoryl)butane of the following formula (1b):

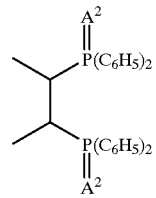

(1b)

wherein $A^2$ is a Group 16 element of the Periodic Table other than oxygen; and an optically active 2,3-O-isopropylidene-2,3-dihydroxy-1,4-bis(diphenylchalcogenophosphoryl)butane of the following formula (1c):

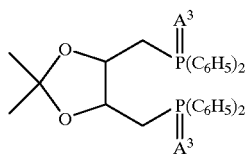

(1c)

wherein $A^3$ is a Group 16 element of the Periodic Table other than oxygen.

In a further aspect, the invention provides a process for the bisalkoxycarbonylation of olefins, which includes reacting an olefin with an alcohol, oxygen and carbon monoxide in the presence of the aforementioned catalyst for the bisalkoxycarbonylation of olefins.

In addition and advantageously, the invention provides a method of producing a succinate derivative, which comprises reacting an olefin with an alcohol, oxygen and carbon monoxide in the presence of the aforementioned catalyst to give a corresponding succinate derivative.

The method just mentioned above may preferably include a method composed of reacting an olefin of the following formula (2):

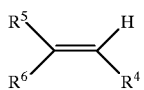

(2)

wherein each of $R^4$, $R^5$ and $R^6$ is, independently, a hydrogen atom, an alkyl group or an aryl group each of which may have a substituent, or a substituted silyl group; at least two of $R^4$, $R^5$ and $R^6$ may together form a ring with the adjacent carbon atom or carbon-carbon double bond, with an alcohol of the following formula (3):

(3)

wherein $R^7$ is an alkyl group, cycloalkyl group or aryl group each of which may have a substituent, oxygen and carbon monoxide to give a succinate derivative of the following formula (4):

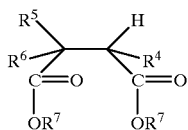

(4)

wherein $R^4$, $R^5$, $R^6$ and $R^7$ have the same meanings as defined above. As the olefin, use maybe made of, for example, any olefin where $R^4$ is a hydrogen atom or an alkyl group which may have a substituent, either one of $R^5$ and $R^6$ is a hydrogen atom or an alkyl group which may have a substituent, and the other is an aryl group which may have a substituent or a substituted silyl group, and $R^4$ and $R^6$ may together form a ring with the adjacent carbon-carbon double bond.

The method of producing a succinate derivative may be a method which includes reacting an olefin capable of forming a chiral compound by reaction, with an alcohol, oxygen and carbon monoxide in the presence of a catalyst containing an optically active phosphine chalcogenide to give a corresponding optically active succinate derivative.

DESCRIPTION OF THE PREFERRED EMBODIMENT

The catalyst for the bisalkoxycarbonylation of olefins according to the invention is composed of a phosphine chalcogenide of the formula (1) and a noble metal compound. In the formula (1), the alkyl groups in $R^1$, $R^2$ and $R^3$ include methyl, ethyl, propyl, butyl, pentyl, hexyl, heptyl, octyl and other straight chain alkyl groups; and isopropyl, isobutyl, sec-butyl, t-butyl and other branched chain alkyl groups. The carbon number of the alkyl group ranges, but not limited to, for example from about 1 to about 20, preferably from about 1 to about 10, and more preferably from about 1 to about 4.

As the aryl group, there may be mentioned, for instance, phenyl group, naphthyl group (1-naphthyl group, 2-naphthyl group) and biphenyl group. The carbon number of the aryl group rages, but not limited to, from about 6 to about 18.

Each of the alkyl groups and aryl groups mentioned above may have a substituent. Examples of the substituent include, aryl groups (e.g., phenyl group, naphthyl group),alkyl groups (methyl, ethyl, propyl, isopropyl, butyl and other $C_1$–$C_4$ alkyl groups), cycloalkyl groups, halogen atoms (e.g., chlorine, bromine, iodine atoms), hydroxyl groups which may be protected with a protective group, mercapto groups which may be protected with a protective group, alkoxy groups (e.g., methoxy, ethoxy, propoxy, isopropoxy, butoxy and other $C_1$–$C_4$ alkoxy groups), alkylthio groups, nitro group, haloalkyl groups (e.g., trifluoromethyl group, chloromethyl group, bromopropyl group and other halo-$C_1$–$C_4$ alkyl groups), carboxy groups which may be protected with a protective group, alkoxycarbonyl groups, aryloxycarbonyl groups, substituted or unsubstituted carbamoyl groups, amino groups which may be protected with a protective group, mono- or di-alkylamino groups, acylamino groups, and acyl groups. As the protective groups, any conventional protective groups in the area of organic synthesis can be employed.

The aforementioned $R^1$, $R^2$ or $R^3$ may be combined, directly or through a bridging group, with one another where the groups to be combined may be attached either to an identical phosphorus atom or to different phosphorus atoms. Examples of such a group formed directly or through a bridging group include methylene group, ethylene group, 1,2-dimethylethylene group, propylene group, butylene group, 2,3-O-isopropylidene-2,3-dihydroxybutylene group, 1,1'-binaphthalen-2,2'-diyl group. Each of these groups may further have a substituent.

The Group 16 element of the Periodic Table shown by A in the formula (1) includes, for instance, oxygen, sulfur, selenium, tellurium, and polonium atoms. Of these elements, oxygen sulfur and selenium atoms are preferred, among which a sulfur atom is particularly desirable.

The phosphine chalcogenide may be whichever of a chiral or achiral compound, and when it is a chiral compound, it may be whichever of an optically active substance or a racemic compound. The phosphine chalcogenide can be immobilized to or supported on an organic or inorganic carrier.

As typical examples of the phosphine chalcogenide, there may be mentioned triphenylphosphine oxide, triphenylphosphine sulfide, triphenylphosphine selenide, tritolylphosphine sulfide, methyldiphenylphosphine sulfide, methyl(1-naphthyl)phenylphosphine sulfide, 1,2-bis(diphenylthiophosphoryl)ethane, 1,4-bis(diphenylthiophosphoryl)butane, 2,2'-bis(diphenylthiophosphoryl)-1,1'-binaphthyl, 2,3-bis (diphenylthiophosphoryl)butane, 2,3-O-isopropylidene-2,3-dihydroxy-1,4-bis(diphenylphosphoryl)butane, 2,3-O-isopropylidene-2,3-dihydroxy-1,4-bis(diphenylthiophosphoryl)butane, 2,3-O-isopropylidene-2,3-dihydroxy-1,4-bis(diphenylselenophosphoryl)butane, and 1,2-bis(diphenylthiophosphorylmethyl)-3,4-bis(2-methoxyphenyl)cyclobutane.

The optically active phosphine chalcogenide includes, for example, optically active substances of the compounds individually of the formulae (1a), (1b) and (1c), and optically active 2,2'-bis(diphenylphosphoryl)-1,1'-binaphthyl, optically active 2,3-bis(diphenylphosphoryl)butane, and optically active 2,3-O-isopropylidene-2,3-dihydroxy-1,4-bis(diphenylphosphoryl)butane.

The Group 16 element of the Periodic Table shown by $A^1$, $A^2$ and $A^3$ in the formulae (1a), (1b) and (1c) includes sulfur, selenium, tellurium, and polonium atoms, for example. Of these elements, a sulfur atom or a selenium atom is preferred, among which a sulfur atom is particularly desirable. A typical example of the optically active 2,2'-bis(diphenylchalcogenophosphoryl)-1,1'-binaphthyl of the formula (1a) includes (R)-2,2'-bis(diphenylthiophosphoryl)-1,1'-binaphthyl. The optically active 2,3-bis(diphenylchalcogenophosphoryl)butane of the formula (1b) typically includes, for example, (2R,3R)-2,3-bis(diphenylthiophosphoryl)butane. As typical examples of the optically active 2,3-O-isopropylidene-2,3-dihydroxy-1,4-bis(diphenylchalcogenophosphoryl)butane of the formula (1c), there may be mentioned (2R,3R)-2,3-O-isopropylidene-2,3-dihydroxy-1,4-bis(diphenylthiophosphoryl)butane, and (2R,3R)-2,3-O-isopropylidene-2,3-dihydroxy-1,4-bis(diphenylselenophosphoryl)butane.

An optically active compound of the formula (1a) can be obtained, for example, by reacting an optically active 2,2'-bis(diphenylphosphino)-1,1'-binaphthyl (BINAP) with an elementary substance of Group 16 element of the Periodic Table at, for example, room temperature in a proper solvent such as an ether, and isolating and purifying the resultant substance by a conventional isolation technique such as column chromatography or recrystallization. An optically active compound of the formula (1b) can be prepared by, for example, reacting an optically active 2,3-bis(diphenylphosphino)butane (Chiraphos) with an elementary substance of Group 16 element of the Periodic Table at, for example, room temperature in a proper solvent such as an ether, and isolating and purifying the resultant substance by a conventional isolation technique such as column chromatography or recrystallization. An optically active substance of the compound of the formula (1c) can be prepared by, for instance, reacting an optically active 2,3-O-isopropylidene-2,3-dihydroxy-1,4-bis(diphenylphosphino)butane (DIOP) with an elementary substance of Group 16 element of the Periodic Table at, for example, room temperature in a proper solvent such as benzene or acetone, and isolating and purifying the resultant substance by a conventional isolation technique such as column chromatography or recrystallization.

The noble metal in the noble metal compound includes, for example, ruthenium, rhodium, palladium, iridium, platinum, silver and gold. As examples of the noble metal compound, there may be mentioned simple substances of such noble metals, noble metal halides (e.g., chlorides, bromides, iodides), inorganic acid salts of noble metals, sulfonates of noble metals (e.g., trifluoromethanesulfonates), carboxylates of noble metals, (e.g., acetates, trifluoroacetates), and complexes of these substances. The noble metal compound (e.g., a simple substance of a noble metal) can be supported on an organic or inorganic carrier. The valency of the noble metal in the noble metal compound may usually be, but not limited to, zero or divalent, trivalent or tetravalent, and typically divalent.

Of these noble metal compounds, palladium compounds are preferable. Typical examples of such palladium compounds include palladium-carbon, palladium-montmorillonite, allyl chloride palladium(II) dimer, palladium(II) halides [e.g., palladium(II) chloride, palladium(II) bromide, palladium(II) iodide], palladium(II) trifluoromethanesulfonate, palladium(II) acetate, palladium (II) trifluoroacetate, and complexes of these compounds. Among them, palladium(II) halides, in particular palladium (II) chloride can advantageously be used.

The phosphine chalcogenide serves as a ligand for the noble metal in the catalyst according to the invention. The invention is, therefore, also directedtonoble metal complexes of the phosphine chalcogenide and to the use of the complexes.

The catalyst of the invention can be composed of the phosphine chalcogenide, the noble metal compound and a co-catalyst. The co-catalyst includes, for instance, copper compounds, iron compounds, manganese compounds, nitrites, and quinones, among which copper compounds are preferred. As examples of the copper compounds, there may be mentioned elementary copper; copper(II) chloride, copper(I) chloride, copper(I) bromide, copper(I) iodide and other copper halides; copper(II) trifluoromethanesulfonate, copper(I) trifluoromethanesulfonate and other copper sulfonates; copper(II) acetate, copper(I) acetate and other copper carboxylates; copper thiocyanates; copper cyanides; and copper complexes. The copper compound (e.g., elementary copper) can be supported by an organic or inorganic carrier. The valency of copper may usually be, but not limited to, monovalent or divalent. Of these copper compounds, copper (I) chloride and other copper(I) halides can advantageously be employed.

According to the process (method) of the invention, an olefin is reacted with an alcohol, oxygen (molecular oxygen) and carbon monoxide in the presence of the aforementioned catalyst. Examples of the olefins include a variety of compounds each having a non-aromatic carbon-carbon double bond, such as aromatic olefins (aromatic vinyl compounds), vinyl silanes, aliphatic olefins, cyclic olefins (e.g., cyclic olefins conjugated with an aromatic ring), and acrylic esters.

Of these olefins, typical examples are of the formula (2). The alkyl group which may have a substituent and the aryl group which may have a substituent in $R^4$, $R^5$ and $R^6$ in the formula (2) include the alkyl groups and aryl groups exemplified in the substituents $R^1$, $R^2$ and $R^3$.

The substituted silyl groups in $R^4$, $R^5$ and $R^6$ include groups of the following formula (5):

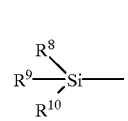
(5)

wherein each of $R^8$, $R^9$ and $R^{10}$ is an alkyl group or aryl group each of which may have a substituent, an alkoxy group or a halogen atom. The alkyl group which may have a substituent and the aryl group which may have a substituent in $R^8$, $R^9$ and $R^{10}$ include the alkyl groups and aryl groups exemplified in the substituents $R^1$, $R^2$ and $R^3$.

Examples of the alkoxy group in $R^8$, $R^9$ and $R^{10}$ include methoxy, ethoxy, propoxy, isopropoxy, butoxy, pentyloxy, hexyloxy and other $C_1$–$C_6$ alkoxy groups. The halogen atom includes, for instance, chlorine, bromine and iodine atoms. As typical examples of the substituted silyl group, there may be mentioned dimethylphenylsilyl group and other tri-substituted silyl groups.

As the ring formed by at least two of $R^4$, $R^5$ and $R^6$ together with the adjacent carbon atom or carbon-carbon double bond, there may be mentioned cyclopentane ring, cyclohexane ring and other cycloalkane rings; cyclopentene ring, cyclohexene ring and other cycloalkene rings; indene ring, 1,2-dihydronaphthalene ring and other condensed hydrocarbon rings formed by condensing an aromatic ring (e.g., benzene ring) to a cycloalkene ring.

Of olefins of the formula (2), preferred are those in which $R^4$ is a hydrogen atom or an alkyl group which may have a substituent (in particular, a hydrogen atom or a $C_1$–$C_4$, alkyl group), either one of $R^5$ and $R^6$ is a hydrogen atom or an alkyl group which may have a substituent (in particular, a hydrogen atom or a $C_1$–$C_4$ alkyl group), the other is an aryl group which may have a substituent or a substituted silyl group, and $R^4$ and $R^6$ may together form a ring with the adjacent carbon-carbon double bond.

The alcohols include a variety of aliphatic alcohols, alicyclic alcohols, aromatic alcohols and phenols. The term "the alcohol" used herein includes phenols as well as other alcohols for the sake of convenience. As the typical examples of the alcohols, there may be mentioned compounds of the formula (3). Examples of the alkyl group which may have a substituent and the aryl group which may have a substituent in $R^7$ in the formula (3) can be exemplified as the alkyl groups and aryl groups indicated in the substituent $R^1$, for example. The cycloalkyl group includes, cyclopropyl, cyclopentyl, cyclohexyl, and cyclooctyl groups. These cycloalkyl groups may have a similar substituent as in the alkyl groups mentioned above.

Practical examples of the alcohols include methanol, ethanol, propanol, isopropyl alcohol, butanol, t-butyl alcohol, octanol and other aliphatic alcohols (e.g., aliphatic alcohols each having about 1 to 20 carbon atoms, preferably about 1 to 10 carbon atoms and more preferably about 1 to 4 carbon atoms); cyclopentanol, cyclohexanol and other alicyclic alcohols; benzyl alcohol and other aromatic alcohols; and phenol, cresol and other phenols.

The amounts of the phosphine chalcogenide of the formula (1), the noble metal compound and co-catalyst used in a reaction of the process (method) according to the invention are not particularly limited and can be properly selected in consideration of the cost efficiency of substrates or reactants, the reactivity or separability from products. By way of illustration, the amount of the phosphine chalcogenide is less than 1 mole (e.g., about 0.01 to 0.5 mole), and preferably about 0.05 to 0.3 mole per mole of the material olefin. The amount of the noble metal compound is less than 1 mole (e.g., about 0.01 to 0.5 mole), and preferably about 0.05 to 0.2 mole per mole of the olefin. The co-catalyst may be used in an amount of, for example, about 0.05 to 3.0 moles, and preferably about 0.5 to 2.0 moles per mole of the olefin.

The amount of the alcohol used in the reaction is, per mole of the olefin, for example equal to or more than 2 moles, and preferably equal to or more than 2.5 moles. The alcohol can also serve as a reaction solvent as well as a reactant.

In addition to the above mentioned alcohols, the reaction solvent includes, but not limited to, acetone and other ketones; tetrahydrofuran and other ethers; benzene, toluene and other aromatic hydrocarbons; hexane, octane and other aliphatic hydrocarbons; acetonitrile, propiononitrile and other nitrites; pyridine, triethylamine and other basic solvents; 1,2-dichloroethane and other halogenated hydrocarbons; amides; and esters. The reaction can be carried out either in the presence of or in the absence of any solvent.

The amount of oxygen is usually equal to or more than 0.5 mole, and that of carbon monoxide is usually equal to or more than 2 moles both per mole of the olefin. Both oxygen and carbon monoxide are generally used in excess with respect to the olefin. The ratio of carbon monoxide to oxygen is for instance such that the former : the latter ranges from about 5:95 to about 95:5, (by mole) and preferably from about 10:90 to about 90:10 (by mole).

The reaction temperature and reaction pressure can suitably be selected in consideration of the reactivity, operativity and cost efficiency. The reaction temperature should fall, for example, in the range from about 0° C. to about 200° C. and preferably from about 20° C. to about 150° C. The reaction is preferably carried out under ambient pressure, but can be conducted under a pressurized condition. The reaction may be carried out in a conventional manner such as in a batch system, semi-batch system or continuous system. After the completion of reaction, reaction products can readily be isolated and purified by a conventional isolation and purification means including filtration, condensation, distillation, extraction, recrystallization or combinations of these isolation means.

According to the above process (method), olefins can be bisalkoxycarbonylated with efficiency. In particular, aromatic olefins and vinylsilanes can give bisalkoxycarbonyl derivatives in high yields. Even from aliphatic terminal olefins, corresponding bisalkoxycarbonyl derivatives can be obtained in high yield. In addition, on reacting cyclic olefins conjugated with an aromatic ring, corresponding cis-diesters (cis-bisalkoxycarbonyl compounds) can selectively obtained.

A reaction according to the process (method) of the invention gives a corresponding succinate derivative (succinic acid ester derivative) from a material olefin in satisfactory yield. By way of example, the reaction of an olefin of the formula (2) with an alcohol of the formula (3), oxygen and carbon monoxide gives a succinate derivative of the formula (4).

Upon the use of a catalyst with the optically active phosphine chalcogenide as a ligand and an olefin, as a material, capable of forming a chiral compound by reaction, a corresponding optically active succinate derivative can be obtained.

The use of a 2-substituted propene derivative (e.g., a 2-silylpropene derivative) or the like as the olefin may result in the formation of 1,3-bisalkoxycarbonyl compound (a glutarate derivative). This is probably because of the elimination and re-insertion of β-hydrido in the reaction process. When an olefin having a hydroxyl group in the molecule (e.g., an olefin having a hydroxyl group at the β- or γ-position carbon atom) is used as a material, an transesterification between one alkoxycarbonyl group of a succinate derivative once formed and the hydroxyl group proceeds to cyclization and hence a corresponding α-alkoxycarbonylmethyllactone is formed. By way of illustration, an olefin having a hydroxyl group at the β-position carbon atom gives a corresponding α-alkoxycarbonylmethyl-γ-butyrolactone derivative. In this case, the use of a catalyst containing an optically active ligand can provide an optically active lactone.

According to the catalyst of the invention, where a noble metal compound is used in combination with a specific ligand, olefins can be bisalkoxycarbonylated with efficiency. The use of the novel phosphine chalcogenide of the invention as a ligand of a catalyst can attain the asymmetric bisalkoxycarbonylation of olefins.

According to the process and method of the invention, corresponding succinate derivatives from individual olefins can be obtained in high yield.

The present invention will be further illustrated in detail with reference to several examples below which are not directed to limiting the scope of the invention. The yields of products in Examples 6 through 8 were determined by gas chromatography. The optical purity of produced optically active substances was determined by high performance liquid chromatography [Daicel Chemical Industries, Ltd., Chiralcel OD, hexane/2-propanol (15:1)].

EXAMPLE 1

Preparation of (2R,3R)-2,3-bis (diphenylthiophosphoryl)butane [(2R,3R)-ChiraphosS$_2$]

Under argon atmosphere, a mixture of (2R,3R)-(+)-2,3-bis(diphenylphosphino)butane [(2R,3R)-Chiraphos] (250 mg, 0.59 mmol), elementary sulfur (121.6 mg, 3.79 mmol), and ether (20 ml) was stirred at room temperature overnight. After removing excess sulfur by chromatography on a silica gel (eluent: hexane), fractions containing the titled compound were collected and condensed. The condensate was then subjected to the purification with a silica gel thin layer chromatography for preparation to give a white crystal of the titled compound (275.5 mg, 0.562 mmol).

$^1$H-NMR (CDCl$_3$) δ: 1.28 (6H, m), 3.47 (2H, m), 7.37–7.88 (20H, m); $^{13}$C-NMR (CDCl$_3$) δ: 9.89, 31.52, 128.46, 128.74, 131.63, 131.97; $^{31}$P-NMR (CDCl$_3$) δ: 53.49; IR (KBr) (cm$^{-1}$): 1440, 1100, 760, 715, 700, 610; mp: 213–214° C.

EXAMPLE 2

Preparation of (2R,3R) -2,3-O-isopropylidene-2,3-dihydroxy-1,4-bis(diphenylthiophosphoryl)butane [(2R,3R)-DIOPS$_2$].

The procedure of Example 1 was repeated to give the titled compound, except that (2R,3R)-(-)-2,3-O-isopropylidene-2,3-dihydroxy-1,4-bis(diphenylphosphino) butane [(2R, 3R)-DIOP] was used instead of (2R,3R)-(+)-2,3-bis(diphenylphosphino)butane.

$^1$H-NMR (CDCl$_3$) δ: 1.11 (6H, s), 2.56 (2H, ddd, J=2.0, 16.8, 13.8 Hz), 2.89 (2H, ddd, J=7.6, 9.2, 16.8 Hz), 4.37–4.44 (2H, m), 7.37–7.49 (12H, m), 7.73–7.89 (8H, m); $^{31}$P-NMR (CDCl$_3$) δ: 40.27; IR (KBr) (cm$^{-1}$): 1440, 1100.

EXAMPLE 3

Preparation of (R)-2,2'-bis(diphenylthiophosphoryl)-1,1'-binaphthyl [(R) -BINAPS$_2$]

The titled compound was prepared in a similar manner as in Example 1, except that (R)-(+)-2,2'-bis (diphenylphosphino)-1,1'-binaphthyl [(R)-BINAP] was used instead of (2R,3R)-(+)-2,3-bis(diphenylphosphino) butane.

$^1$H-NMR (CDCl$_3$) δ: 6.60–6.72 (4H, m), 7.22–7.49 (14H, m), 7.60–7.80 (14H, m); $^{31}$P-NMR (CDCl$_3$) δ: 44.91; IR (KBr) (cm$^{-1}$): 1435, 1095.

EXAMPLE 4

Preparation of (2R,3R)-2,3-O-isopropylidene-2,3-dihydroxy-1,4-bis(diphenylselenophosphoryl)butane Under argon atmosphere, a mixture of (2R,3R)-(-)-2,3-O-isopropylidene-2,3-dihydroxy-1,4-bis (diphenylphosphino)butane [(2R,3R)-DIOP] (995.7 mg, 1.99 mmol), elementary selenium (2.5 g, 31.6 mmol) and benzene (30 ml) was stirred at room temperature for 3 hours. The solid matters were filtered off, and the filtrate was then condensed to give a residue, which was purified by chromatography on a silica gel (eluent: hexane-ethyl acetate= 8:2) and subsequent recrystallization from ethanol to yield a white needle crystal of the titled compound (625.9 mg, 0.95 mmol).

$^1$H-NMR (CDCl$_3$) δ: 1.16 (6H, s), 2.58–2.69 (2H, m), 3.04 (2H, ddd, J=7.6, 10.2, 14.9Hz), 4.44–4.50 (2H, m), 7.37–7.44 (12H, m), 7.73–7.90 (8H, m); $^{31}$P-NMR (CDCl$_3$) δ: 31.96; IR (KBr) (cm$^{-1}$): 1435, 1380, 1235, 1100.

EXAMPLE 5

Preparation of (2R,3R)-2,3-O-isopropylidene-2,3-dihydroxy-1,4-bis(diphenylphosphoryl)butane.

A mixture of (2R,3R)-(-)-2,3-O-isopropylidene-2,3-dihydroxy-1,4-bis(diphenylphosphino)butane [(2R,3R)-DIOP] (957.1mg, 1.92mmol), acetone (20ml) and35% by weight hydrogen peroxide aqueous solution (1 ml) was stirred at room temperature under argon atmosphere for 14 hours. The reaction mixture was condensed to give a solid matter, which after recrystallization from ethanol-water mixture solvent (1 ml: 1.40 ml) afforded the titled compound (933.5 mg, 1.76 mmol).

$^1$H-NMR (CDCl$_3$) δ: 1.11 (6H, s), 2.61 (2H, ddd, J=6.6, 9.2, 15.8 Hz), 2.87 (2H, ddd, J=5.0, 15.8, 15.8 Hz), 4.10–4.22 (2H, m), 7.41–7.53 (12H, m), 7.73–7.82 (8H, m); $^{31}$P-NMR (CDCl$_3$) δ: 30.30; IR (KBr) (cm$^{-1}$): 1435.

EXAMPLE 6

Into a 30-ml two neck eggplant type flask were charged, under argon atmosphere, palladium(II) chloride (17.7 mg, 0.1 mmol), triphenylphosphine sulfide (29.6 mg, 0.1 mmol) and methanol (5 ml), and the mixture was stirred at room temperature for 1 hour. Subsequently, copper(I) chloride (99.0mg, 1 mmol), styrene (155 μl, 1 mmol) and methanol (5 ml) were added to the mixture. The atmosphere was replaced with carbon monoxide-oxygen mixture gas (approximately 1:1 by volume, total pressure: 1 atm) and the mixture was then stirred at room temperature for 3 days. After the completion of reaction, a metal residue was removed by a silica gel short column, and the product was purified through PTLC (hexane:ethyl acetate =4:1) to give dimethyl 2-phenylsuccinate (184.3 mg, 0.83 mmol, yield 83%).

$^1$H-NMR (CDCl$_3$) δ: 2.66 (1H, dd, J=5.28, 16.98), 3.21 (1H, dd, J=9.90, 16.98), 3.64 (3H, s), 4.09 (1H, dd, J=5.28, 9.90), 7.24–7.35 (5H, m); $^{13}$C-NMR (CDCl$_3$) δ: 37.47, 46.93, 51.70, 52.19, 127.53, 127.57, 128.74, 137.52, 171.80, 173.25; IR (cm$^{-1}$): 1740, 1440, 1310, 1160, 1000; mp: 54–56° C.; Colorless crystal.

EXAMPLE 7

The procedure of Example 6 was repeated, except that 0.1 mmol of triphenylphosphine oxide was used instead of triphenylphosphine sulfide, to yield dimethyl 2-phenylsuccinate in a yield of 60%.

EXAMPLE 8

The procedure of Example 6 was repeated, except that 0.1 mmol of triphenylphosphine selenide was used instead of triphenylphosphine sulfide, to give dimethyl 2-phenylsuccinate in a yield of 16%.

EXAMPLE 9

In a similar manner as in Example 6 except that 1 mmol of 4-vinylbiphenyl was used instead of styrene and triphenylphosphine sulfide was employed in an amount of 0.2 mmol, dimethyl 2-(4-biphenyl) succinate was obtained in a yield of 51%.

$^1$H-NMR (CDCl$_3$) δ: 2.71 (1H, dd, J=5.49, 17.03), 3.24 (1H, dd, J=10.16, 17.03), 3.68 (3H, s), 3.70 (3H, s), 4.14 (1H, dd, J=5.49, 10.16), 7.25–7.58 (9H, m); $^{13}$C-NMR (CDCl$_3$) δ: 37.56, 46.72, 51.90, 52.42, 127.01, 127.37, 127.57, 128.11, 128.75, 136.58, 140.46, 140.60, 171.93, 173.36; IR (cm$^{-1}$): 1740, 1490, 1330, 1240, 1160; mp: 103–104° C.; Colorless crystal.

EXAMPLE 10

Dimethyl 2-(p-methoxyphenyl)succinate was obtained in a yield of 82% in a similar manner as in Example 6, except that 1 mmol of p-methoxystyrene was used instead of styrene, and triphenylphosphine sulfide was employed in an amount of 0.2 mmol.

$^1$H-NMR (CDCl$_3$) δ: 2.65 (1H, dd, J=5.49, 16.76), 3.17 (1H, dd, J=9.89, 16.76), 3.66 (6H, s), 3.78 (3H, s), 4.04 (1H, dd, J=5.49, 9.89), 6.83–6.88 (2H, m), 7.17–7.22 (2H, m); $^{13}$C-NMR (CDCl$_3$) δ: 37.65, 46.18, 51.78, 52.25, 55.18, 114.18, 128.70, 129.61, 158.97, 171.96, 173.61; IR (cm$^{-1}$): 2960, 1740, 1515, 1380–1140; Colorless oil.

EXAMPLE 11

Dimethyl 2-(p-chlorophenyl)succinate was afforded in a yield of 59% in a similar manner as in Example 6, except that 1 mol of p-chlorostyrene was used instead of styrene, and triphenylphosphine sulfide was employed in an amount of 0.2 mmol.

$^1$H-NMR (CDCl$_3$) δ: 2.66 (1H, dd, J=5.77, 16.76), 3.18 (1H, dd, J=9.62, 16.76), 3.17 (3H, s), 3.68 (3H, s), 4.07 (3H, dd, J=7.77, 9.62), 7.20–7.32 (4H, m); $^{13}$C-NMR (CDCl$_3$) δ: 37.38, 46.40, 51.89, 52.43, 128.98, 129.08, 133.57, 136.03, 171.61, 172.95; IR (cm$^{-1}$): 1740, 1490, 1440, 1160, 1100; Colorless oil.

EXAMPLE 12

Using 0.99 mmol of allylbenzene instead of styrene and employing triphenylphosphine sulfide in an amount of 0.2 mmol, dimethyl 2-benzylsuccinate was obtained in a yield of 48% in a similar manner as in Example 6.

$^1$H-NMR (CDCl$_3$) δ: 2.40 (1H, dd, J=54.67, 17.03), 2.68 (1H, dd, J=8.79, 17.03), 2.75 (1H, dd, J=7.97, 13.46), 3.05 (1H, dd, J=6.32, 13.46), 3.13 (1H, m), 3.63 (3H, s), 3.66 (3H, s), 7.12–7.32 (5H, m); $^{13}$C-NMR (CDCl$_3$) δ: 34.59, 37.44, 42.73, 51.47, 51.63, 126.43, 128.26, 128.70, 137.82, 171.97, 174.37; IR (cm$^{-1}$) 3100–2850, 1740, 1440, 1300–1140; Colorless oil.

EXAMPLE 13

The procedure of Example 6 was repeated to give dimethyl 2-(o-hydroxybenzyl)succinate in a yield of 70%, except that 1.09 mmol of o-allylphenol was used instead of styrene.

$^1$H-NMR (CDCl$_3$) δ: 2.52 (1H, dd, J=5.77, 16.75), 2.75 (1H, dd, J=7.97, 16.75), 2.82 (1H, dd, J=7.14, 13.73), 3.05 (1H, dd, J=7.14, 13.73), 3.23 (1H, m), 3.65 (3H, s), 3.66 (3H, s), 6.79 (1H, s), 6.78–7.18 (4H, m); $^{13}$C-NMR (CDCl$_3$) δ: 31.89, 35.27, 41.77, 51.99, 52.18, 116.08, 120.31, 124.44, 128.18, 131.04, 154.40, 173.20, 175.61; IR (cm$^{-1}$): 3450, 1740, 1460–1440; Colorless oil.

EXAMPLE 14

Dimethyl cis-1,2-indanedicarboxylate was obtained in a yield of 29% in a similar manner as in Example 6, except that 0.99 mmol of indene was used instead of styrene, triphenylphosphine was employed in an amount of 0.2 mmol and the reaction time after replacement with carbon monoxide-oxygen was changed to 14 days.

$^1$H-NMR (CDCl$_3$) δ: 3.15–3.21 (1H, m), 3.50–3.60 (2H, m), 3.64 (3H, s), 3.73 (3H, s), 4.31–4.33 (1H, m), 7.17–7.37 (4H, m); $^{13}$C-NMR (CDCl$_3$) δ: 34.11, 47.28, 51.94, 52.04, 52.21, 124.82, 124.92, 126.89, 128.19, 139.08, 142.44, 172.39, 172.94; IR (cm$^{-1}$): 3100–2900, 1760–1720, 1590–1420, 1350–1020; Colorless oil.

EXAMPLE 15

Dimethyl cis-1,2-tetralindicarboxylate was obtained in a yield of 35% in a similar manner as in Example 6, except that 1 mmol of 1,2-dihydronaphthalene was used instead of styrene and triphenylphosphine sulfide was employed in an amount of 0.2 mmol.

$^1$H-NMR (CDCl$_3$) δ: 2.08–2.32 (2H, m), 2.58–2.84 (3H, m), 3.48 (3H, s), 3.5 6 (3H, s), 4.05 (1H, d, J=5.22); $^{13}$C-NMR (CDCl$_3$) δ: 20.98, 28.63, 42.16, 45.24, 51.96, 52.07, 125.84, 127.34, 129.23, 129.94, 131.81, 136.35, 172.85, 173.81; IR (cm$^{+1}$): 1740, 1440, 1260–1150; Colorless oil.

EXAMPLE 16

Dimethyl 2-(dimethylphenylsilyl)succinate was obtained in a yield of 91% in a similar manner as in Example 6, except that 1 mmol of dimethylphenylvinylsilane was used instead of styrene and triphenylphosphine sulfide was employed in an amount of 0.2 mmol.

$^1$H-NMR (CDCl$_3$) δ: 0.39 (3H, s), 0.40 (3H, s), 2.25 (1H, dd, J=2.20, 16.21), 2.71 (1H, dd, J=2.20, 11.81), 2.80 (1H, dd, J=11.81, 16.21), 3.60 (6H, s), 7.30–7.60 (5H, m); $^{13}$C-NMR (CDCl$_3$) δ: −5.10, −3.90, 31.22, 32.50, 51.22, 51.67, 127.88, 129.68, 133.66, 135.02, 173.13, 174.59; IR, (cm$^{-1}$): 3100–2900, 1730, 1440, 840; Colorless oil.

EXAMPLE 17

The procedure of Example 6 was repeated, except that 1 mmol of dimethylphenyl(1-propenyl)silane (E/Z=63/37) was used instead of styrene and triphenylphosphine sulfide was employed in an amount of 0.2 mmol, to give dimethyl 2-(dimethylphenylsilyl)-3-methylsuccinate in a yield of 66% (syn/anti 77/23).

$^1$H-NMR (CDCl$_3$) δ: 0.40 (6H, s), 1.05 (major 3H, d, J=7.14), 1.05 (minor 3H, d, J=6.87), 2.60 (major 1H, d, J=10.16), 2.60 (minor 1H, d, J=10.46), 2.80–3.00 (1H, m), 3.54 (3H, s), 3.63 (3H, s), 7.32–7.48 (5H, m); $^{13}$C-NMR (CDCl$_3$) δ: −3.55, −2.51, 17.44, 38.84, 40.71, 51.13, 51.85, 127.76, 127.90, 129.55, 133.82, 134.06, 174.87, 174.50; IR (cm$^{-1}$): 2950, 1740, 1720, 1430, 1160; Colorless oil.

EXAMPLE 18

Using 1 mmol of isopropenyldimethylphenylsilane instead of styrene, and triphenylphosphine sulfide in an amount of 0.2 mmol, dimethyl 3-(dimethylphenylsilyl) glutarate was obtained in a yield of 61% in a similar manner as in Example 6.

$^1$H-NMR (CDCl$_3$) δ: 0.32 (6H, s), 1.91 (1H, m), 2.29 (2H, dd, J=8.79, 15.66), 2.43 (2H, dd, J=5.49, 15.93), 3.58 (6H, s), 7.34–7.56 (5H, m); $^{13}$C-NMR, (CDCl$_3$) δ: −4.68, 18.70, 34.43, 51.50, 127.84, 129.82, 133.92, 136.46, 173.62; IR (cm$^{-1}$) : 2960, 1740, 1440; Colorless oil.

EXAMPLE 19

Except using 1 mmol of o-chlorostyrene instead of styrene, and triphenylphosphine sulfide in an amount of 0.2 mmol, dimethyl 2-(o-chlorophenyl)succinate was obtained in a yield of 26% in a similar manner as in Example 6.

$^1$H-NMR (CDCl$_3$) δ: 2.68 (1H, dd, J=5.22, 17.03), 3.15 (1H, dd, J=9.89, 17.03), 3.69 (3H, s), 3.71 (3H, s), 4.61 (1H, dd, J=5.22, 9.89), 7.18–7.45 (4H, m); $^{13}$C-NMR (CDCl$_3$) δ: 36.43, 43.98, 51.89, 52.45, 127.24, 128.81, 128.90, 129.97, 133.64, 135.63, 171.71, 172.83; IR (cm$^{-1}$): 1740, 1440, 1170; Colorless oil.

EXAMPLE 20

The procedure of Example 6 was repeated to give methyl 1-(3-isochromanonyl)acetate in a yield of 25%, except that 1.01 mmol of o-vinylbenzyl alcohol was used instead of styrene and triphenylphosphine sulfide was employed in an amount of 0.2 mmol.

$^1$H-NMR (CDCl$_3$) δ: 3.15 (2H, ddd, J=6.59, 16.75, 32.41), 3.76 (3H, s), 3.76–3.80 (1H, m), 4.09–4.14 (1H, m), 5.35 (2H, dd, J=13.74, 37.09), 7.17–7.69 (4H, m); $^3$C-NMR (CDCl$_3$) δ: 32.00, 41.07, 52.15, 69.36, 123.94, 124.93, 127.35, 128.90, 171.82, 171.89; IR (cm$^{-1}$): 1760–1720, 1440, 1150; Colorless oil.

EXAMPLE 21

Except that 1.01 mmol of 5-phenyl-1-pentene was used instead of styrene, methyl 3-methoxycarbonyl-6-phenylhexanoate was obtained in a yield of 28% in a similar manner as in Example 6.

$^1$H-NMR (CDCl$_3$) δ: 1.52–2.00 (4H, m), 2.20–2.95 (5H, m), 3.66 (3H, s), 3.69 (3H, s), 7.12–7.32 (5H, m); $^{13}$C-NMR (CDCl$_3$) δ: 28.65, 31.41, 35.47, 35.76, 40.93, 51.71, 51.78, 125.78, 128.26, 128.30, 128.34, 172.29, 175.24; IR (cm$^{-1}$): 1740, 910, 740; Colorless oil.

EXAMPLE 22

Except using 1 mmol of t-butyl acrylate instead of styrene, and triphenylphosphine sulfide in an amount of 0.2 mmol, the procedure of Example 6 was repeated to give dimethyl 2-(t-butoxycarbonyl)succinate in a yield of 34%.

EXAMPLE 23

Into a 30-ml two necked eggplant type flask were charged, under argon atmosphere, palladium(II) chloride (8.9 mg, 0.05 mmol), (2R,3R)-2,3-bis(diphenylthiophosphoryl) butane [(2R,3R)-ChiraphosS$_2$] (27.0 mg, 0.06mmol), copper (II) acetate (142.0 mg, 0.78 mmol), 1,1-diphenyl-3-buten-1-ol (111.6 mg, 0.5 mmol) and methanol (4 ml). After replacing the inside atmosphere with a gaseous mixture of carbon monoxide-oxygen (approximately 1:1 by volume, total pressure: 1 atm), the charged was stirred at room temperature for 3 days. After the completion of reaction, a metal residue was removed by a silica gel short column, and the product was purified through PTLC (hexane:ethyl acetate=4:1) to give 2-(methoxycarbonylmethyl)-4,4-diphenyl-γ-butyrolactone (100.7 mg, 0.32 mmol, yield 65%, optical purity 14% ee).

EXAMPLE 24

Into a 30-ml two necked eggplant type flask were placed, under argon atmosphere, palladium(II) trifluoroacetate (16.2 mg, 0.05 mmol), (1S,2S,3S,4S)-1,2-bis (diphenylthiophosphorylmethyl)-3,4-bis(2-methoxyphenyl) cyclobutane [(1S,2S,3S,4S)-CDPS$_2$] (40.5 mg, 0.06 mmol) and methanol (2 ml), and the mixture was stirred at room temperature for 1 hour. To the mixture were then added copper(II) acetate (138.6 mg, 0.76 mmol), 1,1-diphenyl-3-buten-1-ol (112.0 mg, 0.5 mmol) and methanol (2 ml), the inner atmosphere was replaced with a gaseous mixture of carbon monoxide-oxygen (about 1:1 by volume, total pressure: 1 atm), and the charged was stirred at room temperature for 3 days. After the completion of reaction, a metal residue was removed by a silica gel short column, and the product was purified through PTLC (hexane:ethyl acetate=4:1) to afford 2-(methoxycarbonylmethyl)-4,4-diphenyl-γ-butyrolactone (123.9 mg, 0.40 mmol, yield 80%, optical purity 36% ee).

EXAMPLE 25

Into a 30-ml two necked eggplant type flask were placed, under argon atmosphere, palladium(II) chloride (8.1 mg, 0.05 mmol), (1S,2S,3S,4S)-1,2-bis (diphenylthiophosphorylmethyl)-3,4-bis(2-methoxyphenyl) cyclobutane [(1S,2S,3S,4S)-CDPS$_2$] (35.8 mg, 0.05 mmol) and methanol (2 ml), and the mixture was stirred at room temperature for 1 hour. To the mixture were then added copper(I) chloride (75.8 mg, 0.77 mmol), 1,1-diphenyl-3-buten-1-ol (112.0 mg, 0.5 mmol) and methanol (2 ml), the inner atmosphere was replaced with a gaseous mixture of carbon monoxide-oxygen (about 1:1 by volume, total pressure: 1 atm), and the charged was stirred at room temperature for 3 days. After the completion of reaction, a metal residue was removed by a silica gel short column, and the product was purified through PTLC (hexane:ethyl acetate=4:1) to give 2-(methoxycarbonylmethyl)-4,4-diphenyl-γ-butyrolactone (143.7 mg, 0.46 mmol, yield 86%, optical purity 35% ee).

EXAMPLE 26

Into a 30-ml two necked eggplant type flask were placed, under argon atmosphere, palladium(II) chloride (17.7 mg, 0.10 mmol), (1S,2S,3S,4S)-1,2-bis (diphenylthiophosphorylmethyl)-3,4-bis(2-methoxyphenyl) cyclobutane [(1S,2S,3S,4S) -CDPS$_2$] (72.9 mg, 0.10 mmol) and methanol (5 ml), and the mixture was stirred at room temperature for 1 hour. To the mixture were then added copper(I) chloride (99.3 mg, 1.00 mmol), dimethylphenylvinylsilane (163.5 mg, 1.01 mmol) and methanol (5 ml), the inner atmosphere was replaced with a gaseous mixture of carbon monoxide-oxygen (about 1:1 by volume, total pressure: 1 atm), and the charged was stirred at room temperature for 3 days. After the completion of reaction, a metal residue was removed by a silica gel short column, and the product was purified through PTLC (hexane:ethyl acetate=4:1) to afford dimethyl 2-(dimethylphenylsilyl)succinate (193.8 mg, 0.69 mmol, yield 69%, optical purity 18% ee).

EXAMPLE 27

Into a 30-ml two necked eggplant type flask were placed, under argon atmosphere, palladium(II) chloride (17.7 mg, 0.10 mmol), (R)-2,2'-bis(diphenylthiophosphoryl)-1,1'-binaphthyl [(R)-BINAPS$_2$] (68.7 mg, 0.10 mmol) and methanol (5 ml), and the mixture was stirred at room temperature for 1 hour. To the mixture were then added copper(I) chloride (99.0 mg, 1.00mmol), dimethylphenylvinylsilane (166.8 mg, 1.03 mmol) and methanol (5 ml), the inner atmosphere was replaced with a gaseous mixture of carbon monoxide-oxygen (about 1:1 by volume, total pressure: 1 atm), and subsequently the charged was stirred at room temperature for 3 days. After the completion of reaction, a metal residue was removed by a silica gel short column, and the product was purified through PTLC (hexane:ethyl acetate=4:1) to afford dimethyl 2-(dimethylphenylsilyl)succinate (195.2 mg, 0.70 mmol, yield 70%, optical purity 24% ee).

EXAMPLE 28

Into a 30-ml two necked eggplant type flask were placed, under argon atmosphere, palladium(II) chloride (17.8 mg, 0.10 mmol), methyldiphenylphosphine sulfide (46.5 mg, 0.20 mmol) and methanol (5 ml), and the mixture was stirred at room temperature for 1 hour. To the mixture were then added copper(I) chloride (99.8 mg, 1.00 mmol), styrene (104.0 mg, 1.00 mmol) and methanol (5 ml), the inner atmosphere was replaced with a gaseous mixture of carbon monoxide-oxygen (about 1:by volume, total pressure: 1 atm), and subsequently the charged was stirred at room temperature for 3 days. After the completion of reaction, a metal residue was removed by a silica gel short column, and the product was purified through PTLC (hexane:ethyl acetate=4:1) to give dimethyl 2-phenylsuccinate in a yield of 17%.

EXAMPLE 29

Into a 30-ml two necked eggplant type flask were placed, under argon atmosphere, palladium(II) chloride (26.4 mg, 0.15 mmol), methyl(1-naphthyl)phenylphosphine sulfide (85.6 mg, 0.30 mmol) and methanol (5 ml), and the mixture was stirred at room temperature for 1 hour. To the mixture were then added copper(I) chloride (148.0 mg, 1.50 mmol), styrene (156.0 mg, 1.50 mmol) and methanol (5 ml), the inner atmosphere was replaced with a gaseous mixture of carbon monoxide-oxygen (about 1:1 by volume, total pressure: 1 atm), and subsequently the charged was stirred at room temperature for 3 days. After the completion of reaction, a metal residue was removed by a silica gel short column, and the product was purified through PTLC (hexane:ethyl acetate=4:1) to give dimethyl 2-phenylsuccinate in a yield of 36%.

EXAMPLE 30

Into a 30-ml two necked eggplant type flask were placed, under argon atmosphere, palladium(II) chloride (0.1 mmol), (R)-2,2'-bis(diphenylthiophosphoryl)-1,1'-binaphthyl [(R)-BINAPS$_2$] (0.1 mmol) and methanol (5 ml), and the mixture was stirred at room temperature for 1 hour. To the mixture were then added copper(I) chloride (1 mmol), styrene (1 mmol) and methanol (5 ml), the inner atmosphere was replaced with a gaseous mixture of carbon monoxide-oxygen (about 1:1 by volume, total pressure: 1 atm), and subsequently the charged was stirred at room temperature for 3 days. After the completion of reaction, a metal residue was removed by a silica gel short column, and the product was purified through PTLC (hexane:ethyl acetate=4:1) to afford dimethyl 2-phenylsuccinate (yield 48%, optical purity 8% ee).

EXAMPLE 31

Dimethyl 2-phenylsuccinate (yield 41%, optical purity 24% ee) was obtained in a similar manner as in Example 30, except that 0.1 mmol of (2R,3R)-2,3-O-isopropylidene-2,3-dihydroxy-1,4-bis(diphenylthiophosphoryl)butane [(2R, 3R)-DIOPS$_2$] was used instead of (R)-2,2'-bis(diphenylthiophosphoryl)-1,1$^1$-binaphthyl.

EXAMPLE 32

Dimethyl 2-phenylsuccinate (yield 68%, optical purity 30% ee) was obtained in a similar manner as in Example 30, except that 0.1 mmol of (2R,3R)-2,3-bis(diphenylthiophosphoryl)butane [(2R,3R)-ChiraphosS$_2$] was used instead of (R)-2,2'-bis(diphenylthiophosphoryl)-1, 1'-binaphthyl.

As many apparently widely different embodiments of this invention may be made without departing from the spirit and scope thereof, it is to be understood that the invention is not limited to the specific embodiments thereof except as defined in the appended claims.

What is claimed is:

1. A catalyst comprising a palladium(II) halide and a phosphine chalcogenide of the following formula (1):

wherein each of $R^1$, $R^2$ and $R^3$ is, independently, an alkyl group or an aryl group each of which may have a substituent selected from the group consisting of aryl groups, alkyl groups, cycloalkyl groups, halogen atoms, hydroxyl groups which may be protected with a protective group, mercapto groups which may be protected with a protective group, alkoxy groups, alkylthio groups, nitro group, haloalkyl groups, carboxy groups which may be protected with a protective group, alkoxycarbonyl groups, aryloxycarbonyl groups, substituted or unsubstituted carbamoyl groups, amino groups which may be protected with a protective group, mono- or di-alkylamino groups, acylamino groups, and acyl groups;

A is an element selected from the group consisting of a sulfur atom or a selenium atom; and $R^1$, $R^2$ or $R^3$ may be combined, directly or through a bridging group, with one another where the groups to be combined may be attached either to the same phosphorus atom or to a different phosphorus atom.

2. The catalyst according to claim 1, wherein said phosphine chalcogenide is one member selected from the group consisting of, triphenylphosphine sulfide, triphenylphosphine selenide, 2,2'-bis(diphenylthiophosphoryl)-1,1'-binaphthyl, 2,3-bis(diphenylthiophosphoryl)butane and 2,3-O-isopropylidene-2,3-dihydroxy-1,4-bis (diphenylthiophosphoryl)butane.

3. The catalyst according to claim 1, further comprising a co-catalyst.

4. The catalyst according to claim 3, wherein said co-catalyst is a copper compound.

5. The catalyst according to claim 3, wherein said co-catalyst is a copper(I) halide.

6. The catalyst according to claim 1, wherein aryl group in the substituent is selected from the group consisting of phenyl and naphthyl; alkyl group in the substituent is selected from the group consisting of methyl, ethyl, propyl, isopropyl, butyl and other $C_1$–$C_4$ alkyl groups; halogen atom is selected from the group consisting of chlorine, bromine, and iodine; alkoxy groups is selected from the group consisting of methoxy, ethoxy, propoxy, isopropoxy, butoxy and other $C_1$–$C_4$ alkoxy groups; and haloalkyl group is selected from the group consisting of trifluoromethyl, chloromethyl, bromopropyl and other halo-$C_1$–$C_4$ alkyl groups.

* * * * *